US00PP22588P3

(12) United States Plant Patent
Bacon

(10) Patent No.: US PP22,588 P3
(45) Date of Patent: Mar. 20, 2012

(54) PEACH TREE NAMED 'SUPECHSEVENTEEN'

(50) Latin Name: *Prunus persica*
Varietal Denomination: Supechseventeen

(75) Inventor: Terry Bacon, Bakersfiled, CA (US)

(73) Assignee: Sun World International, LLC, Bakersfield, CA (US)

( * ) Notice: Subject to any disclaimer, the term of this patent is extended or adjusted under 35 U.S.C. 154(b) by 26 days.

(21) Appl. No.: 12/924,362

(22) Filed: Sep. 24, 2010

(65) Prior Publication Data

US 2011/0179537 P1 Jul. 21, 2011

Related U.S. Application Data

(60) Provisional application No. 61/336,224, filed on Jan. 19, 2010.

(51) Int. Cl.
*A01H 5/00* (2006.01)

(52) U.S. Cl. ..... Plt./197

(58) Field of Classification Search ..... Plt./197
See application file for complete search history.

*Primary Examiner* — Annette Para
(74) *Attorney, Agent, or Firm* — Knobbe, Martens, Olson & Bear, LLP

(57) ABSTRACT

A new and distinct peach tree variety, *Prunus persica,* cv. 'Supechseventeen' is characterized by fruit with large size, dark over-color and an early harvest.

1 Drawing Sheet

Latin name of the genus and species claimed: *Prunus persica.*

Variety denomination: 'Supechseventeen'.

BACKGROUND AND SUMMARY OF THE INVENTION

This invention relates to the discovery and asexual propagation of a new and distinct variety of peach, *Prunus persica* cv. 'Supechseventeen'. The new variety was first hybridized in 2001 and selected in 2003 by Terry Bacon as breeder number: 'PE386'. The new variety was first evaluated by Terry Bacon near Wasco, Calif. in Kern County. The variety 'Supechseventeen' was originated by hybridization.

The new variety 'Supechseventeen' is characterized by its large size, dark over-color and early harvest.

The seed parent is 'Supechsix' (the subject of U.S. Plant Pat. No. 11,631), and the pollen parent is '91-006C' (an unpatented Sun World peach). The parent varieties were first crossed in February 2001, with the date of planting of the progeny being February 2002, and the date of first flowering being February 2003. The new peach variety 'Supechseventeen' was first asexually propagated by Terry Bacon near Wasco, Kern County, Calif. in January 2005, by budding.

The new variety 'Supechseventeen' is distinguished from its seed parent, 'Supechsix', in that the fruit of the new variety ripens about five days later than that of 'Supechsix' and has darker over-color. The fruit of the new variety 'Supechseventeen' is larger in diameter than that of 'Supechsix', at about 65 mm in comparison to 64 mm.

The fruit of the new variety 'Supechseventeen' is distinguished from that of its pollen parent, '91-006C', in that the fruit of the new variety ripens about four days later than that of '91-006C' and has melting flesh while the fruit of '91-006C' has non-melting flesh. The fruit of the new variety 'Supechseventeen' is also larger in diameter than that of '91-006C', at about 65 mm in comparison to 63 mm.

The fruit of the new variety 'Supechseventeen' ripens at nearly the same time as that of 'Super Rich' (U.S. Plant Pat. No. 9,860), but is larger in size at about 65 mm in comparison with 63 mm of 'Super Rich'. The fruit of the new variety also has darker over-color than that of 'Super Rich'. The fruit of the new variety is also similar in appearance and shape to the fruit of 'Crimson Lady' (U.S. Plant Pat. No. 7,953), but its harvest starts about 20 days earlier.

The new variety 'Supechseventeen' has been shown to maintain its distinguishing characteristics through successive asexual propagations by, for example, budding.

BRIEF DESCRIPTION OF THE PHOTOGRAPH

The accompanying color photographic illustration shows typical specimens of the foliage and fruit of the present new peach variety 'Supechseventeen'. The illustration shows the upper and lower surface of the leaves, exterior views of the fruit and the pit, and a sectional view of a fruit divided across its suture plane to show flesh color, pit cavity and the stone remaining in place. The photographic illustration was taken shortly after the fruit was picked (shipping ripe) and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England.

The descriptive matter which follows pertains to 4 year old 'Supechseventeen' plants on Nemared (unpatented) rootstock, grown in the vicinity of Wasco, Kern County, Calif., during 2009, and is believed to apply to plants of the variety grown under similar conditions of soil and climate elsewhere.

TREE

General: (Measurements taken on 4 year old tree unless otherwise noted.)

*Size.*—Medium. Normal for most peach varieties. Reaches a height of approximately 3 meters with normal pruning.

*Spread.*—Normal for most peach varieties. Approximately 3 meters.

*Vigor.*—Moderately vigorous; growth of about 1.8 to about 2 meters high during the first growing season.

*Growth.*—Semi-upright.

*Productivity.*—Productive. Fruit set is usually two or more times desired amount for marketable size fruit; thinning and spacing of fruit is necessary.

*Form.*—Vase formed.

*Bearer.*—Regular.

*Fertility.*—Self-fertile.

*Canopy density.*—Dense.

*Hardiness.*—Hardy in all fruit growing areas of California; winter chilling requirement is approximately 350 hours at or below 7.2 C.

*Disease resistance/susceptibility.*—No specific testing for relative plant disease resistance/susceptibility has been undertaken. Under close observation in Kern County, Calif., no particular plant/fruit disease resistance/susceptibility has been observed.

Trunk: (Measurements at approximately 30 cm above soil line.)

*Diameter.*—Approximately 17 cm, varies with soil type, fertility, climatic conditions and cultural practices.

*Texture.*—Medium shaggy, increases with age of tree.

*Trunk color.*—Outer bark about Light Greyed-green 197D to about Dark Greyed-green 197A; inner bark about Dark Greyed-orange 177A to about Medium Greyed-orange 174B.

Branches: (Measurements at approximately 90 cm above soil line.)

*Size.*—Diameter ranges from approximately 9 cm.

*Texture.*—Medium shaggy; increasing with tree age.

*Color.*—Branches vary from about Light Greyed-green 197D to about Medium Greyed-orange 166D.

*Number of lenticels.*—Medium.

*Lenticels density.*—Approximately 2-4 per $cm^2$.

*Lenticels color.*—About Medium Greyed-orange 166D.

*Lenticels size.*—Medium.

*Lenticels length.*—Approximately 3 mm.

*Lenticels width.*—Approximately 1.5 mm.

Flowering shoots: (Data taken in July at midpoint of previous season shoots.)

*Size.*—Average diameter approximately 5 mm.

*Color.*—Topside: About Dark Greyed-orange 166B. Underside: About Light Yellow-green 144C.

*Internode length.*—Medium; approximately 11-16 cm. Midway on flowering shoot.

*Flowering shoot lenticels.*—Sparse. Color: About Light Greyed-green 196A. Diameter: Approximately 0.3 mm.

*Flowering shoot leaf buds.*—Shape: Elliptic to conical. Width: Approximately 3 mm. Length: Approximately 4 mm. Color: About Medium Greyed-green 197C.

*Flowering shoot flower buds.*—Shape: Conical. Width: Approximately 25 mm. Length: Approximately 4 mm. Color: About Medium Greyed-green 197C. Number of buds per node: Usually 2.

*Density of buds.*—Medium.

*Flower bud distribution.*—Generally isolated in groups of 2 on one year old shoots.

*Ratio of wood (leaf) buds to flowering shoots.*—1/2.

FOLIAGE

Leaves:

*Size.*—Medium.

*Average length.*—Medium; approximately 12-16 cm.

*Average width.*—Medium; approximately 3-4 cm.

*Thickness.*—Medium.

*Color.*—Upper surface: About Dark Yellow-green 146B. Lower surface: About Medium Yellow-green 146C.

*Form.*—Lanceolate.

*Tip.*—Cuspidate.

*Base.*—V-shaped.

*Margin.*—Crenate.

*Venation.*—Pinately veined.

*Vein color.*—About Light Yellow-green 144C to about Medium Greyed-orange 176D.

*Surface texture.*—Smooth.

*Leaf blade (Ratio of length to width).*—Medium; about 4/1.

*Shape in the cross section.*—Concave.

*Profile.*—Up folded.

*Leaf blade tip.*—Curved downwardly.

*Undulation of margin.*—Slight.

Petiole:

*Average length.*—Medium; approximately 13 mm.

*Average diameter.*—Approximately 2 mm.

*Color.*—About Medium Yellow-green 144A.

Stipules:

*Number/leaf bud.*—Approximately 2.

*Typical length.*—Approximately 7 mm.

*Color.*—About Dark Greyed-orange 176A when dry.

*Persistence.*—Falls off.

Leaf glands:

*Form.*—Reniform.

*Average number.*—Between about 0 and 6; usually between about 2 and 4.

*Position.*—On both leaf base and petiole, alternate.

*Average size.*—Medium; approximately 1 by 1.5 mm.

*Color.*—About Medium Yellow-green 144B.

FLOWERS

General:

*Flower blooming period.*—First bloom: Approximately Feb. 12, 2009. Full bloom: Approximately Feb. 17, 2009.

*Time of bloom.*—Early.

*Duration of bloom.*—Medium; approximately 12 days.

*Diameter of fully opened flower.*—Medium, approximately 40 mm.

*Flower aroma.*—Slight aroma.

*Shape.*—Rosaceous.

Peduncle:

*Length.*—Medium; approximately 4 mm.

*Diameter.*—Slender; approximately 1.5 mm.

*Color.*—About Medium Yellow-green 144A.

*Pubescence.*—Absent.

Petals:

*Number.*—5.

*Arrangement.*—Slightly overlapping.

*Length.*—Approximately 15 mm.

*Diameter.*—Approximately 9 mm.

*Shape.*—Oval.
*Apex shape.*—Rounded.
*Base shape.*—Narrows, cuneate.
*Color.*—About Light Red-purple 62C, becoming darker over time.
*Surface texture.*—Smooth.
*Margins.*—Slightly undulating.
*Claw length.*—Short.
*Margin waviness.*—Weak.
*Base angle.*—Medium.
*Division of upper margin.*—Entire.
*Pubescence of inner surface.*—Absent.
*Pubescence of outer surface.*—Absent.

Sepals:
*Number.*—5.
*Length.*—Approximately 5 mm.
*Diameter.*—Approximately 3 mm.
*Shape.*—Triangular.
*Color.*—About Medium Red-purple 64B outside surface.
*Surface texture.*—Smooth.
*Margins.*—Entire.
*Positioning.*—Touching petals when opened.
*Pubescence of inner surface.*—Absent.
*Pubescence of outer surface.*—Absent.

Stamens:
*Number.*—Many; usually 38-48.
*Average length.*—Approximately 12 mm.
*Filament color.*—About Light Red-purple 62C, darkening to Medium Red-purple 64B as flower ages.
*Anther color.*—About Medium Red-purple 61B.
*Flower pollen color.*—About Dark Yellow-orange 22A when dried.
*Position.*—Perigynous.

Pistil:
*Number.*—Usually one.
*Average length.*—Approximately 18 mm.
*Ovary diameter.*—Approximately 1.5 mm.
*Pubescence.*—None.
*Stigma extension in comparison to anthers.*—Usually with and above.
*Frequency of supplementary pistils.*—Few.

Receptacle:
*Depth.*—Medium
*Pubescence of inner surface.*—Absent.
*Pubescence of outer surface.*—Absent.

Ovary:
*Pubescence.*—Slight.
*Density of hairs.*—Dense.

FRUIT

General: (Description taken at the Sun World Research and Development Center near Wasco, Kern County, Calif.)
*Harvest.*—Date of first pick: Approximately May 4, 2009. Date of last pick: Approximately May 12, 2009.

Maturity when described: Firm-mature.
Season ripening: Very early.
Position of maximum diameter: Towards the middle.
Symmetry about the suture: Somewhat symmetric.

Size:
*Length* (*stem end to apex*).—Approximately 66 mm.
*Diameter in line with suture plane.*—Approximately 65 mm.
*Diameter perpendicular to suture plane.*—Approximately 65 mm.
*Average weight.*—Approximately 135 gm.

Form:
*Viewed from apex.*—Rounded, nearly symmetrical.
*Viewed from side, facing suture.*—Rounded, nearly symmetrical.
*Viewed from side, perpendicular to suture.*—Rounded, nearly symmetrical.

Apex shape: Rounded.

Fruit stem cavity:
*Shape.*—Rounded.
*Depth.*—Medium; approximately 0.8 cm.
*Breadth.*—Approximately 1.5 cm.
*Width.*—Medium.

Fruit stem:
*Length.*—Approximately 9 mm.
*Diameter.*—Approximately 2.5 mm.
*Color.*—About Medium Greyed-orange 164B.
*Adherence to stone.*—Medium.

Fruit skin:
*Thickness.*—Medium.
*Adherence to flesh.*—Strong.
*Surface texture.*—Medium.
*Pubescence.*—None.
*Bloom.*—Slight.
*Ground color.*—About Dark Yellow-orange 17D when mature.
*Overcolor.*—About Medium Red 47B.
*Taste.*—Neutral.
*Reticulation.*—Absent.
*Roughness.*—Absent.
*Tenacity.*—Tenacious to flesh.
*Tendency to crack.*—Slight, in wet season.

Flesh:
*Ripens.*—Evenly.
*Texture.*—Firm, melting.
*Fibers.*—Few.
*Flavor.*—Mild.
*Brix.*—Approximately 12°.
*Juice.*—Moderate.
*Aroma.*—Slight.
*Color.*—About Medium Yellow-orange 15C when mature.
*Acidity.*—Medium.
*Eating quality.*—Good.
*Stone/flesh ratio.*—About 1/4.
*Firmness.*—Firm.

Pit cavity size:
*Length* (*diameter in line with suture plane*).—Approximately 29-33 mm.
*Diameter perpendicular to suture plane.*—Approximately 19 mm.
*Color.*—About Medium Yellow-orange 15C.

Fruit use: Fresh market.
Fruit shipping and keeping quality: Good, holds well in cold storage and maintains good firmness and eating quality; minimal bruising and scarring in packing and shipping trials.
Suture line: Inconspicuous.

Stone: (Measurements taken on dried stones.)
*Stone freeness.*—Clings over entire surface.
*Degree of adherence to flesh.*—Medium.
*Stone size.*—Size compared to Fruit: Medium. Length (Diameter in line with suture plane): Approximately 29-33 mm. Diameter perpendicular to suture plane: Approximately 19 mm. Width of Stalk End: Medium; approximately 3 mm. Angle of Stalk end: Right angle. Hilum: Oval.

*Stone form.*—Viewed from side: Oval. Viewed from ventral side: Flattened. Viewed from stem end: Oval, nearly symmetrical.

*Stone shape.*—Base shape: Nearly straight. Apex shape: Pointed.

*Stone surface.*—Pitted throughout.

*Stone halves.*—Nearly symmetric.

*Stone ridges.*—Rounded continuous.

*Stone outgrowing keel.*—Partially developed.

*Stone tendency to split.*—Slight in wet season.

*Stone color.*—About Medium Greyed-orange 166C when dried.

*Position of maximum.*—Toward middle.

*Ventrical edge.*—Medium.

*Dorsal edge.*—Narrow grooves, interrupted.

What is claimed is:

1. A new and distinct peach tree as herein described and illustrated.

* * * * *

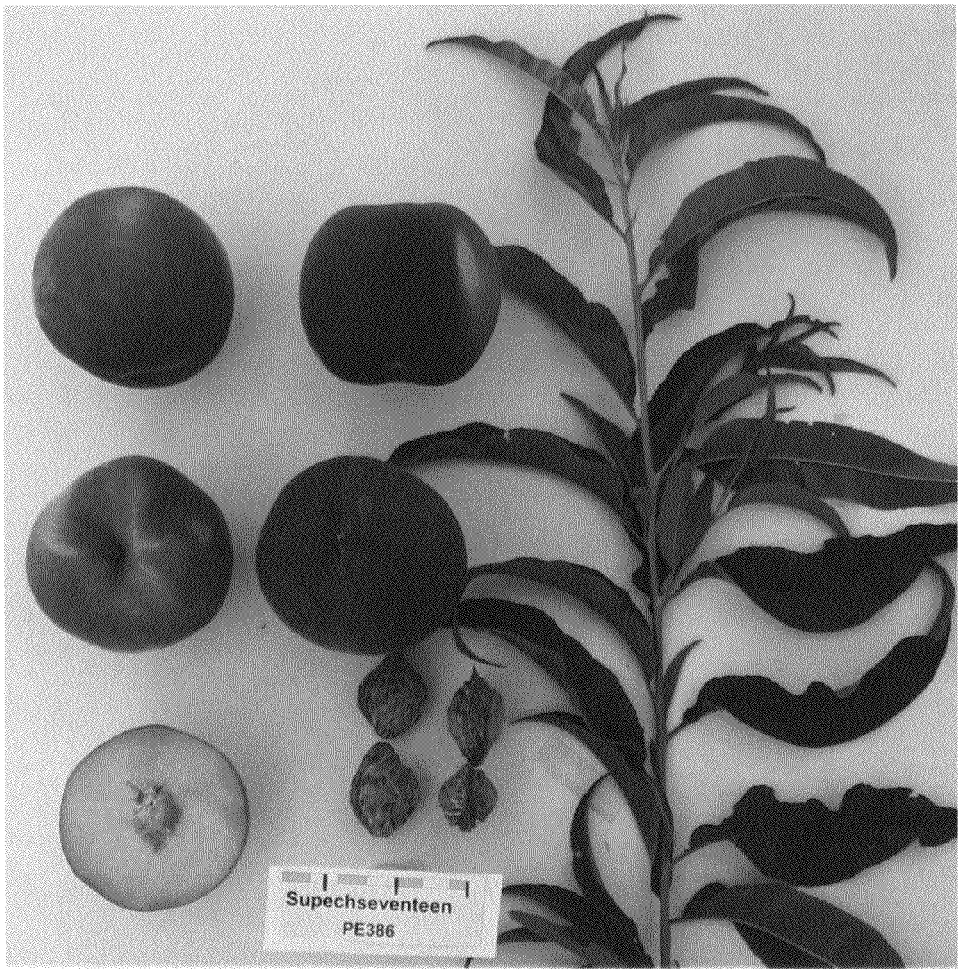
Supechseventeen
PE386